US007393548B2

(12) United States Patent
Friedman

(10) Patent No.: US 7,393,548 B2
(45) **Date of Patent: *Jul. 1, 2008**

(54) NANO OIL IN GLYCERIN EMULSION

(75) Inventor: Doron I. Friedman, Karme Yosef (IL)

(73) Assignee: J.P. M.E.D. Ltd. (IL)

( * ) Notice: Subject to any disclaimer, the term of this patent is extended or adjusted under 35 U.S.C. 154(b) by 476 days.

This patent is subject to a terminal disclaimer.

(21) Appl. No.: 10/394,111

(22) Filed: Mar. 21, 2003

(65) Prior Publication Data

US 2004/0067244 A1 Apr. 8, 2004

Related U.S. Application Data

(63) Continuation-in-part of application No. 09/700,862, filed as application No. PCT/IL00/00142 on Mar. 9, 2000, now Pat. No. 6,544,530, application No. 10/394, 111, filed on Mar. 21, 2003, and a continuation-in-part of application No. PCT/IL01/00826, filed on Dec. 8, 2000.

(30) Foreign Application Priority Data

| | | | |
|---|---|---|---|
| Mar. 22, 1999 | (IL) | ..................................... | 129102 |
| Sep. 21, 2000 | (IL) | ..................................... | 138616 |

(51) Int. Cl.

| | |
|---|---|
| ***A61K 36/00*** | (2006.01) |
| ***A61K 8/02*** | (2006.01) |
| ***A61K 8/73*** | (2006.01) |

(52) U.S. Cl. ..................... 424/725; 424/401; 424/70.13

(58) Field of Classification Search ................. 424/401, 424/725, 70.13
See application file for complete search history.

(56) References Cited

U.S. PATENT DOCUMENTS

| | | | | | |
|---|---|---|---|---|---|
| 5,329,881 | A | | 7/1994 | O'Rourke | |
| 5,350,773 | A | * | 9/1994 | Schweikert et al. | 514/763 |
| 5,459,127 | A | * | 10/1995 | Felgner et al. | 514/7 |
| 5,494,938 | A | * | 2/1996 | Kawa et al. | 514/786 |
| 5,607,622 | A | * | 3/1997 | Ueda et al. | 516/76 |
| 6,004,566 | A | | 12/1999 | Friedman et al. | |
| 6,019,967 | A | * | 2/2000 | Breton et al. | 424/130.1 |
| 6,066,328 | A | | 5/2000 | Ribier et al. | |
| 6,193,987 | B1 | | 2/2001 | Harbeck | |
| 6,207,699 | B1 | * | 3/2001 | Rothman | 514/419 |

FOREIGN PATENT DOCUMENTS

| | | | | |
|---|---|---|---|---|
| EP | 361 928 | A2 | | 4/1990 |
| JP | 09-111237 | A | | 4/1997 |
| WO | WO96/21422 | | * | 7/1996 |
| WO | WO 00/56346 | A1 | | 9/2000 |
| WO | WO 02/24152 | A2 | | 3/2002 |

* cited by examiner

*Primary Examiner*—Christopher R Tate
*Assistant Examiner*—Randall Winston
(74) *Attorney, Agent, or Firm*—Townsend and Townsend and Crew, LLP

(57) ABSTRACT

The invention provides a cosmetic or pharmaceutical composition in the form of an oil-in-glycerin emulsion, with mean droplet size below one micron, comprising a continuous glycerin phase, at least one vegetable oil comprising an internal phase, at least one emulsifying stabilizer, and at least one bioactive compount comprising at least one hydrophobic, moiety within its structure, wherein the composition facilitates stratum-corneum penetration and dermal penetration of said bioactive compound.

13 Claims, No Drawings

NANO OIL IN GLYCERIN EMULSION

The present application is a continuation-in-part of U.S. Ser. No. 09/700,862, filed Jan. 22, 2001, the U.S. national phase of PCT IL00/00142, filed Mar. 9, 2000, which designates the U.S. and was published in English, which derives priority under 35 USC §119 from IL129,102, filed Mar. 22, 1999. The present application is also a continuation-in-part of PCT/IL01/00826, filed Sep. 2, 2001, which designates the U.S. and was published in English, and which derives priority under 35 USC §119 from IL 138,616, filed Sep. 21, 2000. The priority applications are incorporated by reference in their entirety for all purposes.

The present invention relates to oil-in-glycerin emulsion compositions, with sub-micron range, mean droplets size, for topical application, that facilitating stratum-corneum penetration, used for intra-dermal and trans-dermal applications, for administering various pharmaceutical or cosmetic agents having at least one hydrophobic moiety.

BACKGROUND OF INVENTION

Most drugs are not amenable to transdermal mode of administration due to the well-known barrier properties of the skin. Molecules moving from the environment into and through intact skin must first penetrate the stratum-corneum. It is the stratum-corneum that presents the greatest barrier to absorption of topical compositions or transdermally administered drugs. The stratum-corneum, the outer horny layer of the skin, is a complex structure of compact keratinized cell remnants separated by lipid domains. Compared to the oral or gastric mucous, the stratum-corneum is much less permeable to outside molecules.

The flux of a drug across the skin can be increased by changing either a) the resistance (the diffusion coefficient), or b) the driving force (the solubility of the drug in the stratum-corneum and consequently the gradient for diffusion). Many enhancer compositions have been developed to change one or more of these factors, and are known in the art. U.S. Pat. Nos. 4,006,218, 3,551,154 and 3,472,931, for example, respectively describe the use of dimethylsulfoxide (DMSO), dimethyl formamide (DMF) and N,N-dimethylacetamide (DMA) to enhance the absorption of topically applied drugs through the stratum corneum. Combinations of enhancers consisting of diethylene glycol monoethyl or monomethyl ether with propylene glycol monolaurate and methyl laurate are disclosed in U.S. Pat. No. 4,973,468 as enhancing the transdermal delivery of steroids such as progestogens and estrogens. A dual enhancer consisting of glycerol monolaurate and ethanol for the transdermal delivery of drugs is shown in U.S. Pat. No. 4,820,720. U.S. Pat. No. 5,006,342 lists numerous enhancers for transdermal drug administration consisting of fatty acid esters or fatty alcohol ethers of C.sub.2 to C.sub.4 alkanediols, where each fatty acid/alcohol portion of the ester/ether is of about 8 to 22 carbon atoms. U.S. Pat. No. 4,863,970 shows penetration-enhancing compositions for topical application comprising an active permeant contained in a penetration-enhancing vehicle containing specified amounts of one or more cell-envelope disordering compounds such as oleic acid, oleyl alcohol, and glycerol esters of oleic acid; a C.sub.2 or C.sub.3 alkanol and an inert diluents such as water.

The use of sorbitan esters of long chain aliphatic acids as skin permeation enhancers is disclosed in U.S. Pat. Nos. 5,122,383; 5,212,199 and 5,227,169. Skin permeation enhancement using aliphatic alcohol esters of lactic acid is disclosed in U.S. Pat. No. 5,154,122, World Patent 95/09006 and in Dohi et al., Enhancing Effects of Myristyl Lactate and Lauryl Lactate on Percutaneous Absorption of Indomethacin, Chem Pharm. Bull. 38 (October 1990) 2877-2879. U.S. Pat. No. 5,314,694 also makes reference to the use of esters of fatty acid alcohols, i.e. lauryl alcohol and lactic acid as a permeation enhancer component.

World Patent 96/37231 teaches the use of acyl lactylates as permeation enhancers for drug delivery purposes. This patent is specific to esters of fatty acids and lactic acid such as caproyl lactylic acid and lauroyl lactylic acid. It is stated that the salt form of acyl lactylates are not effective as permeation enhancers.

Many of the enhancer systems possess negative side effects such as toxicity, skin irritation and incompatibility with the drugs or other ingredients making up the transdermal system. U.S. Pat. No. 4,855,294 discloses compositions for reducing skin irritation caused by drug/enhancer compositions having skin irritation properties comprising a percutaneously absorbable drug, a binary enhancer composition consisting of a solvent and a cell envelope disordering compound, combined with an amount of glycerin sufficient to provide an anti-irritating effect.

Skin permeation enhancement due to fatty acid sucrose esters is disclosed in U.S. Pat. No. 4,940,586. Penetration enhancement resulting from combining free base and acid addition salt combinations of drugs is taught in U.S. Pat. No. 4,888,354. Enhancement of drugs by means of sub-saturation in a carrier is disclosed in U.S. Pat. No. 5,164,190.

U.S. Pat. Nos. 6,066,328 and 5,658,575 "Cosmetic or dermatological composition comprising an oil-in-water emulsion based on oily globules provided with a lamellar liquid crystal coating and made of—at least one lipophilic surface-active agent, at least one hydrophilic surface-active agent, and at least one fatty acid, the coated oily globules having a mean diameter of less than 500 nanometermeters, preferably less than 200 nanometermeters, and the oily phase contains a basic agent in the dissolved state, exhibit good skin and hair penetration"

U.S. Pat. No. 6,004,566 disclose oil-in-water sub micron emulsions that enhance absorption due reduction of mean particles size to below half a micron. However, two components are needed for stabilizing the emulsion, an emulsifying stabilizer and a surfactant.

All patents, mentioned above, do not disclose oil-in-glycerin type composition or homogenized oil-in-glycerin emulsions stabilized with fatty acid/s and carbohydrate conjugates. Many of the enhancer chemicals listed above were not exploited due to dose dependent skin adverse reaction that limits their clinical use. Alcohols, azones, fatty acids such as oleic acid and other suggested skin permeation enhancers are also causing skin damage or irritation or sensitization.

Oil-in-glycerin emulsions have been claimed in PCT/IL00/00142. Said specification describes a composition of matter comprising a stable oil-in-glycerin emulsion containing at least one oil, at least one emulsifying stabilizer and glycerin. Said invention relates to oil-in-glycerin emulsions in which the oil is the internal phase and the glycerin is the external, continuous phase. However, this patent do not refers to the unexpected observation of facilitated stratum-corneum penetration and method of intra-dermal and transdermal medication which involves the transport of drugs or cosmetics active agent into and/or through the skin.

It would be desirable to have an enhancer composition which not only enabled the passage of drug compositions across the skin barrier but which was also beneficial to the moisturization, stability and overall vitality of the epidermis. Skin having properly moisturized stratum corneum is smooth to the touch, flexible and elastic due to the presence of sufficient bound water. A 1% variation of water content may be enough to modify skin elasticity and permeability. Suitable skin hydration-also promotes transdermal delivery of drugs through the stratum corneum.

To be considered useful, a permeation enhancer should have the ability to enhance the permeability of the skin for at least one and preferably a significant number of agents. More importantly, it should be able to enhance the skin permeability such that the agent delivery rate from a reasonably sized system (preferably 5-50 cm.sup.2) is at therapeutic levels. Additionally, the enhancer when applied to the skin surface should be non-toxic, non-irritating on prolonged exposure and under occlusion, and non-sensitizing on repeated exposure. Preferably, it should be odorless and capable of delivering agents without producing burning or tingling sensations.

It is the objective of the present invention to furnish a carrier system for bioactive agents comprising at least one hydrophobic moiety, whereas an enhanced absorption is obtained while avoiding the side effects associated with many of the chemical enhancers such as alcohols or sodium lauryl sulfate and also provide for safe and biodegradable product and also free of synthetic polymers and also free of preservatives.

The advent of genetic engineering and especially recombinant DNA technology has made available many biologically active peptides. The peptides include human insulin, human growth hormone, bovine growth hormone, endorphins and enkephalines, calcitonin, interferons, interleukins and other lymphokines, TPA, vasopressin, oxytocin and many others.

Peptides are made up of groups of amino acid linked together by amide bonds. The distinction between peptides and proteins, which also are groups of amino acids linked by amide bonds, is somewhat vague, but usually they are separated by size or number of amino acids in the chain.

Use of these biologically active peptides in medical practice is not so simple. Because of the nature of the peptide bond, they are not stable in the acidic conditions of the stomach and thus have very poor oral activity. The most common route of administering biologically active peptides is by injection by the intravenous or I.M. or S.C. routes, which are not amenable to outpatient treatment.

In addition to the acid instability of peptides, enzymes in the body known as peptidases break down these peptides, rapidly destroying their biological activity, some peptides, e.g., Angiotensin I and bradykinin, have a half-life of less than 30 seconds. A transdermal delivery system for peptides would be ideal in many ways.

Unexpectedly, it has now been discovered that bioactive agents having at least one hydrophobic moiety such as phytomedicine, peptides, drugs and cosmeceuticals formulated in homogenized oil in glycerin permeation enhancer compositions of mean droplet size of below one micron better penetrate the stratum corneum natural protective layer of the skin and show higher dermal concentration and/or biological dermal effect. Bioactive agents that will not be biodegraded in the dermis and that will accumulate in the dermis, will finally diffuse into the circulation and will result in systemic effect via transdermal route.

SUMMARY OF THE INVENTION

According to the present invention there is provided a cosmetic or pharmaceutical composition in the form of an oil-in-glycerin emulsion with mean droplet size below one micron, comprising a continuous glycerin phase at least one vegetable oil comprising an internal phase at least one emulsifying stabilizer and at least one bioactive compound comprising at least one hydrophobic moiety within its structure, wherein said composition facilitates stratum-corneum penetration and dermal penetration of said bioactive compound.

More specifically, the present invention provides a cosmetic or pharmaceutical composition in the form of an oil-in-glycerin emulsion, with mean droplet size below one micron, comprising:

a) a continuous glycerin phase;

b) at least one vegetable oil comprising an internal phase;

c) at least one emulsifying stabilizer; and d) at least one bioactive compount comprising at least one hydrophobic, moiety within its structure, wherein the composition facilitates stratum-corneum penetration and dermal penetration of said bioactive compound.

As stated, the compositions of the present invention are especially preferred for trans-dermal, administration of bioactive compounds and intra-dermal administration of bioactive compounds.

In preferred embodiments of the present invention said bioactive compound is hydrophobic or amphiphilic and is predominantly associated with the oily internal phase droplets.

Preferably, in the compositions of the present invention, the mean droplet size is between 100 and 1,000 nanometers.

In preferred embodiments of the present invention the emulsifying stabilizer is made by condensation of at least one fatty acid or alcohol with a carbohydrate or poly-carbohydrate.

In the compositions of the present invention, preferably oil is present in an amount ranging from about 0.1-40 wt/wt % and most preferred are compositions wherein said oil is present in an amount ranging from about 1-20 wt/wt %.

In preferred embodiments said emulsifying stabilizer is preferably present in an amount ranging from about 0.1-10 wt/wt % and preferably said bioactive component is present in an amount ranging from about 0.1-20 wt/wt %.

In especially preferred embodiments of the present invention said continuous glycerin phase comprises at least 50% glycerin.

Preferably said emulsifying stabilizer is capable of forming liquid crystal lamellar phase.

In preferred embodiments of the present invention said emulsifying stabilizer is selected from the group consisting of cetearyl glucoside, sucrose esters and sorbitan esters.

In other preferred embodiments of the present invention said glycerin constitutes a continuous phase of said emulsion and a minor portion of water is included in said glycerin phase.

Preferably said oil-in-glycerin emulsion is self-preserving and free of microbial preservatives.

In preferred embodiments of the present invention the mean nanometer droplet size is obtained solely by a process of mechanical mixing or high shear homogenization.

Preferably said bioactive component is selected from the group consisting of a botanical extract, a drug, a peptide, a polypeptide, a nucleotide, and a glycolipid and preferably said vegetable oil is a vegetable tryglyceride of a regular or a medium chain triglyceride.

The present invention provides a stable oil-in-glycerin nanometer emulsion that can perform as an adequate storage and delivery vehicle bringing forth enhanced stratum-corneum and or skin penetration properties for bioactive ingredients having at least one hydrophobic moiety, including peptides, drugs, phytochemicals and oligonucleotides or liposacharides.

Thus, in one embodiment, this invention comprises an admixture of a pharmacologically active agent having at least one hydrophobic moiety formulated in a penetration enhancer oil in glycerin emulsion composition for the administration of therapeutically effective amounts of said active agent.

In another embodiment, the invention provides a method for enhancing the rate of penetration of a pharmacologically active agent having at least one hydrophobic moiety through the stratum-corneum, wherein the method comprises administering to the skin of the patient undergoing treatment a mixture of the pharmacologically active agent in the permeation enhancer composition as described herein.

In preferred embodiments of the present invention the emulsifying stabilizer is of vegetable origin made by condensation of at least one fatty acid or alcohol with a carbohydrate or poly-carbohydrate.

In especially preferred embodiments of the present invention there is provided a systemic pharmaceutical composition in the form of an oil-in-glycerin emulsion with mean droplet size below one micron for trans-dermal administration, comprising:

a) a continuous glycerin phase, b) at least one vegetable oil comprising an internal phase, c) at least one emulsifying stabilizer wherein said emulsifying stabilizer is capable of forming a liquid crystal lamellar phase and the emulsifying stabilizer is made by condensation of at least one fatty acid or alcohol with a hydrophilic molecule, d) at least one bioactive pharmaceutical compound comprising at least one hydrophobic moiety within its structure, and low water solubility or hydrophobic properties, wherein said composition facilitates stratum corneum penetration and dermal penetration of said bioactive pharmaceutical compound.

DETAILED DESCRIPTION OF THE INVENTION

"Penetration enhancement" or "permeation enhancement" as used herein relates to an increase in the permeability of skin to a pharmacologically active agent, having at least one hydrophobic moiety or increase in the rate at which the agent permeates into and through the skin.

The term "transdermal" drug delivery as used herein is intended to denote the term in its conventional sense, i.e., to indicate delivery of a drug by passage through the skin and into the blood stream. "Topical" drug delivery is used to mean local administration of a topical drug as in, for example, the treatment of various skin disorders.

The terms, vegetable or botanical are interchangeable and are aimed to describe non-animal origin in respect to the origin of the oil-in-glycerin emulsion ingredients.

The term HLB is an arbitrary scale from 0 to 40 depicting the Hydrophilic/Lipophilic Balance of a surfactant. Products with low HLB are more oil soluble. High HLB represents good water solubility. Note that HLB is a numerically calculated number based on the surfactants molecular structure. It is not a measured parameter.

It has been unexpectedly found that such bioactive agents incorporated in the present homogenized nanometer oil-in-glycerin penetration enhancer composition as formed from components A, B and C above of mean droplets size of below 1 micron, better penetrates into and through the skin to obtain significant dermal or transdermal activity. Even peptides of MW larger then 1,000 or with 20 or more amino acids, have been unexpectedly found to pass the stratum-corneum into the skin inner layers and also sub-dermal.

It has also been unexpectedly found that it is possible to obtain nanometer oil-in-glycerin emulsion by plain high shear homogenization in contrast to the common art, where a high-pressure homogenization is required to reduce emulsions droplet to below one micron. Moreover, single pass in high pressure homogenization is enough to further reduce particles size. Also, oil-in-glycerin emulsion show lower distribution of sizes around mean in comparison to regular oil-in-water emulsions, especially less energy, time and pressure is required to obtain uniform particle size.

In preferred embodiments of the present invention the following quantities are preferable:

a) said vegetable oil is present in an amount ranging from about 1-30 wt/wt %, or from 2-20 wt/wt %;

b) said emulsifying stabilizer is present in an amount ranging from about 0.1-20 wt/wt %, or from about 0.1-5 wt/wt %; and c) said bioactive component is present in an amount ranging from about 0.1-20 wt/wt %.

In a most preferred embodiment said emulsifying stabilizer is biodegradable (i.e., degradable in the human body and the environment) and is substantially free of polyoxyethylene or propylene glycols and is preferably of botanical origin.

A hydrophobic moiety in the bioactive agent may be a benzene or cyclic ring or heterocyclic backbone or hydrocarbon side chain, etc.

In an even further preferred embodiment of the present invention said glycerin constitutes a continuous phase of said emulsion and a minor portion of water is included in said glycerin phase.

Example of vegetable oils are: isopropyl miristate, jojoba oil, almond oil, avocado oil, coconut oil, capric-caprylic tryglyceride of fractionated coconut oil, nutmeg oil, castor oil, olive oil and oleic acid, soybean oil etc. The oil may be saponifiable or unsaponifiable and liquid or solid at room temperature.

In a preferred embodiment there is provided a composition of matter comprising oil-in-glycerin emulsion and bioactive agent, wherein the bioactive component is selected from the group consisting of a phytochemical (plant origin or plant extract) or drug or a peptide or nucleotide or glycolipid or cosmeceutics anti-histamines, anti-inflammatory agents, analgesics, anesthetics, antiperspirants, anti-dandruffs, antimicrobial agents, astringents, counter-irritants, depigmenting agents, bleaching agents, and steroids.

In a preferred embodiment of this invention said emulsifying stabilizer is selected from the group consisting of at least one fatty acid or fatty alcohol condensation with natural hydrophilic molecule to form an amphiphilic and surface active agent with HLB of 5 to 16, that is the emulsifying stabilizer. The hydrophilic molecule may be selected from carbohydrates or amino acids or amine containing carbohydrate molecules prevailing in the vegetable kingdom. The carbohydrate may be a saccharide or an acid such as tartaric or citric acid and the like. The amine carbohydrate molecule is one having a natural carbohydrate backbone and at least one nitrogen atom such as amine or tertiary amine or amide and at least one alcohol or carboxylic acid moiety, for example: betain or choline.

In a preferred embodiment of this invention said emulsifying stabilizer is selected from the group consisting of at least one fatty acid condensation with a carbohydrate or with a polycarbohdrate, wherein said carbohydrate is a saccharide, a disaccharide or a polysaccharide, said surfactant and stabilizer is a liquid crystal lyothropic lamellar forming amphiphil, and said liquid-crystal-forming surfactant and stabilizer is a sucrose ester or cetearyl glucoside.

In a preferred aspect of the invention, the combination of an oil-in-glycerin emulsion and a bioactive agent facilitates the dispersion of a water insoluble bioactive component in a biocompatible, safe and convenient dosage form, while avoiding the disadvantages associated with classical vehicles comprising ionic or polymeric and synthetic surfactants or alcohols or preservatives.

Practically there is no need to include anti-microbial preservatives in oil-in-glycerin emulsions, since oil-in-glycerin emulsions are self preserving and passing the preservative efficacy test also named challenge test as specified in USP or BP or CTFA guidance.

The oil-in-glycerin emulsions are pleasant for use on the skin and on mucous membranes such as the oral cavity, ears and scalp and are also ingestable when prepared from food grade ingredients. Additionally, the emulsions of the present invention are well accepted organoleptically and physiologically, hence, offering good patient compliance. Stable oil-in-glycerin emulsions offering water free surrounding with potential for stabilizing bioactive agents that are sensitive to water and that are rapidly degrading in aqueous medium.

As will be realized, the present invention provides an emulsion which may be produced alcohol and/or water free, has a prolonged shelf life and improved heat stability for withstanding elevated temperatures during a long period of time. Furthermore, the oil-in-emulsion resists sub-zero temperatures, it is stable upon freezing and does not break at minus 20° C. Thaw of oil-in-glycerin emulsions is simple and does not affect original properties.

Oil-in-glycerin emulsions are easily prepared. It is possible to produce coarse oil-in-glycerin emulsions of 5 to 10 microns droplet size with simple stirring and without resort to the use of high shear mixers. It is also easy to control droplet size by the utilization of appropriate mixing equipment and energy input. Fine oil-in-glycerin emulsions, having a mean droplet size of 1 to 5 micron, are achieved with a conventional "Silverson" type mixer at moderate speed and a short duration of mixing. High shear homogenizer mixing is sufficient to obtain emulsions containing 0.5 to 1 microns mean droplets size, consequent high pressure homogenization produces 0.5 to 0.1 mean particle size.

Typical oil-in-glycerin emulsions are characterized by having viscosity of 5,000 to 25,000 centipoise and newtonian flow. Viscosity may be reduced by the addition of water. The oil-in-glycerin emulsion viscosity may be controlled by addition of viscosity forming agents, such as, carbomers, carbopol, cellulose derivatives or natural gums, such as xanthan gum or colloidal fumed silica. Also, the same additives easily achieve non-neutinian characteristics.

Oil-in-glycerin emulsions are suitable for use in humans and animals, on skin, scalp, mucous membrane, ear instillation, oral rinse, and f. Buccal transmucosal applications The oil-in-glycerin emulsions are basically newtonian and flow easily out of any commercial consumer product orifice opening or dropper. Oil-in-glycerin emulsions may be packaged in glass, aluminum or plastic containers or designed into patch device.

A bioactive agent may be a phytochemical, drug, cosmeceutical, peptide, oligonucleotide or liposaccharide or combinations thereof.

The botanical extract of the present invention may have anti-inflammatory, anti-allergic, anti-bacterial, anti-parasitic, anti-viral, immunity modulation and/or anti-oxidant, anti-psoriatic, sun-protecting, anti-aging, rejuvenating, anti-wrinkle or anti-cancer properties.

Example of botanical bioactive agents, are: polyphenols, isoflavones, resveratrol, soy isoflavones, grape seed extract polyphenols, curcumin, epigenin. Anti-inflammatory plant extracts such as aloe vera, echinacea and chamomile hammamekis extracts, anti-psoriatic such as chinese zizipus jujuba. Astringents such as hammamelis anti bacterial such as artemisia, chamomile, golden seal. Immune modulators such as echinacea, anti-aging or anti-cancer or anti-photo damage, anti-inflammatory such as feverfew parthenolides, rejuvenation agents, carotenoids, beta-carotene, lycopene, tocopheryl and retinol.

The term "drug" or "pharmacologically active agent" as used herein is intended to mean a compound or composition of matter which, when administered to an organism (human or animal) induces a desired pharmacological and/or physiologic effect by local and/or systemic action. In general, the terms include the therapeutic or prophylactic agents in all major therapeutic or prophylactic areas of medicine. Examples of drugs useful in conjunction with the present invention include: anti-infectives such as antibiotics and anti-viral agents; analgesics and analgesic combinations; anorexics; antihelminthics; antiarthritics; antiasthmatic agents; anticholinergic agents; anticonvulsants; antidepressants; antidiabetic agents; antidiarrheals; antihistamines; anti-inflammatory agents, antimigraine preparations; anti-motion sickness drugs; antinauseants; antineoplastics; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and anti-arrhythmics; antihypertensives; diuretics; vasodilators including general coronary, peripheral and cerebral; central nervous system stimulants; cough and cold preparations, including decongestants; steroids; hypnotics; immunosuppressives; muscle relaxants; parasympatholytics; psychostimulants; sedatives; and tranquilizers. For purposes of the aforementioned definition, "drugs" as used herein also include locally administered topical medicaments such as antibacterial agents, antifungals, antimicrobials, cutaneous growth enhancers, antipsoriatics, anti-acne medicaments, and the like.

The invention is thus, in one embodiment, a method for enhancing the rate of penetration of a pharmacologically active agent into and/or through the skin, wherein the method involves co-administration of the agent through a predetermined area of intact skin, and for a predetermined period of time, of the selected agent in a permeation enhancer composition comprising oil in glycerin emulsion.

A transdermal delivery system for the administration of drug and enhancer composition as described herein may take the form of a depot-type device, matrix or laminate-type device, bandages, or the like. A preferred transdermal delivery system for use herein is a laminated composite that contains one or more drug/permeation enhancer reservoirs, a backing layer and, optionally, one or more other layers, e.g., additional drug and/or enhancer reservoirs, release rate controlling membranes, or the like (as those skilled in the art of transdermal delivery will readily appreciate).

In these composites, the backing layer will function as the primary structural element of the device and provide the device with much of its flexibility. This layer also serves as a protective covering to prevent loss of drug and enhancer via transmission through the upper surface of the device. The backing layer may also be used to impart the device with a desirable or necessary degree of occlusivity, which in turn causes the area of skin on which the device is placed to become hydrated. The backing is preferably made of a sheet or film of a flexible elastomeric material. Suitable, flexible elastomeric materials include polyether block amide copolymers, polyurethanes, silicone elastomers, rubber-based polyisobutylene, styrene, polyethylene, polypropylene, polyesters, or the like. The preferred polymer used for the backing will depend primarily on the particular pharmacologically active agent incorporated into the device.

Prior to use, the laminated composite also includes a release liner layer. Just prior to use, this layer is removed from the device to expose the basal surface of the device. The release liner will normally be made from a drug/enhancer impermeable material that is inherently "strippable" or rendered so by techniques such as silicone or fluorocarbon treatment.

Preferred daily dosages obtained with the present methods and systems will, similarly, vary with the drug administered. The targeted daily dosage will depend on the individual being treated, the indication addressed, the length of time the individual has been on the drug, and the like.

In still another embodiment, the invention comprises a drug delivery device in the form of a patch administering a pharmacologically active agent through a selected area of skin. The device is preferably in the form of a laminated composite that includes a drug reservoir layer containing both the agent to be administered and the permeation enhancer composition of the invention.

Oil-in-glycerin emulsion may comprise also known in the art additives, such as anti-oxidants, coloring, flavoring and fragrance.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLES

The oily and glycerin phases are heated separately to 70° C. until all ingredients melt and are well dissolved. The phases are combined while mixing. Mixing may be performed with any mixer, blender, homogenizer, etc. which is used for producing emulsions. Oil-in-glycerin emulsions may also be prepared by heating all the ingredients, including oil, glycerin and emulsifying stabilizers, except for heat sensitive bioactives, in a single batch, mixing to achieve melting of solids and with continued mixing until cooled to room temperature, with the addition of any heat sensitive bioactives to the cooling mixture.

Example 1

Oil-in-Glycerin Emulsion; Plain Semi-Solid Base

| Ingredient | % W/W |
|---|---|
| Glycerin | 84.0 |
| Medium chain tryglyceride (MCT) oil | 12.0 |
| Cetearyl-glucoside (Montanov 68) | 4.0 |

TABLE 1

Mean particle size of example 1 formula at various mixing methods.

| Mixing method | Mean particle size | Method |
|---|---|---|
| Magnetic stirrer | 5 microns | Light microscope |
| High shear homogenizer | 0.5 microns | Laser light scattering |
| High pressure homogenizer | 0.2 microns | Laser light scattering |

Example 2

Oil-in-Glycerin Emulsion; Plain Liquid Base

| Ingredient | % W/W |
|---|---|
| Glycerin | 88.0 |
| Medium chain tryglyceride (MCT) oil | 10.0 |
| Sucrose ester (Sisterna S50C) | 2.0 |

TABLE 2

Mean particle size formula of example 2 at various mixing methods.

| Mixing method | Mean particle size | Method |
|---|---|---|
| Magnetic stirrer | 5 microns | Light microscope |
| High shear homogenizer | 0.7 microns | Laser light scattering |
| High pressure homogenizer | 0.4 microns | Laser light scattering |

Example 3

Oil-in-Glycerin Emulsion; Plain Liquid Base

| Ingredient | % W/W |
|---|---|
| Glycerin | 83.5 |
| Medium chain tryglyceride (MCT) oil | 15.0 |
| Sucrose ester (Sisterna S50) | 1.0 |
| Mono-di-glycerides | 0.5 |

Example 4

Oil-in-Glycerin Emulsion; Plain Semi-Solid Base

| Ingredient | % W/W |
|---|---|
| Glycerin | 65.0 |
| Medium chain tryglyceride (MCT) oil | 10.0 |
| Cetearyl-glucoside (Montanov 68) | 5.0 |
| Water | 20.0 |

Example 5

Oil-in-Glycerin Emulsion; Isoflavones

| Ingredient | % W/W |
|---|---|
| Glycerin | 83.5 |
| Medium chain tryglyceride (MCT) oil | 10.0 |
| Cetearyl-glucoside (Montanov 68) | 5.0 |
| Vit E | 0.5 |
| Soy Isoflavones | 1.0 |

Example 6

Oil-in-Glycerin Emulsion; Genistein Semi-Solid Base

| Ingredient | % W/W |
|---|---|
| Glycerin | 63.5 |
| Medium chain tryglyceride (MCT) oil | 10.0 |
| Cetearyl-glucoside (Montanov 68) | 5.0 |
| Vit E | 0.5 |
| Genistein | 0.5 |
| Water | 20.0 |

TABLE 3 example 6 formula dermal tissue levels of Genistein at different mixing methods.

| Mixing method | Rats dermal Genistein levels, at 30, 60 and 120 minutes | Method |
|---|---|---|
| Magnetic stirrer | Lowest | HPLC |
| High shear homogenizer | Highest | HPLC |

Example 7

Oil-in-Glycerin Emulsion; Resveratrol

| Ingredient | % W/W |
|---|---|
| Glycerin | 83.5 |
| Medium chain tryglyceride (MCT) oil | 10.0 |

-continued

| Ingredient | % W/W |
|---|---|
| Cetearyl-glucoside (Montanov 68) | 5.0 |
| Vit E | 0.5 |
| Grape seeds extract with resveratrol | 0.5 |

Example 8

Oil-in-Glycerin Emulsion; Polyphenols

| Ingredient | % W/W |
|---|---|
| Glycerin | 63.5 |
| Medium chain tryglyceride (MCT) oil | 10.0 |
| Cetearyl-glucoside (Montanov 68) | 5.0 |
| Vit E | 0.5 |
| Green tea polyphenols extract | 0.5 |
| Water | 20.0 |

Example 9

Oil-in-Glycerin Emulsion; Polyphenols Semi-Solid Base

| Ingredient | % W/W |
|---|---|
| Glycerin | 81.5 |
| Almond oil | 4.0 |
| Jojoba oil | 6.0 |
| Sorbitan monooleate (Span 80) | 4.0 |
| Cetearyl alcohol | 3.0 |
| Vit E | 0.5 |
| Green tea polyphenols extract | 1.0 |

Example 10

Oil-in-Glycerin Emulsion; CoQ10

| Ingredient | % W/W |
|---|---|
| Glycerin | 83.5 |
| Medium chain tryglyceride (MCT) oil | 10.0 |
| Cetearyl-glucoside (Montanov 68) | 5.0 |
| Vit E | 0.5 |
| Coenzyme Q10 | 0.5 |

Example 11

Oil-in-Glycerin Emulsion; CoQ10 Semi-Solid Base

| Ingredient | % W/W |
|---|---|
| Glycerin | 63.0 |
| Medium chain tryglyceride (MCT) oil | 10.0 |
| Sucrose ester HLB 12 | 4.0 |
| Sucrose ester HLB 15 | 2.0 |
| Vit E | 0.5 |
| Coenzyme Q10 | 0.5 |
| Water | 20 |

Example 12

Oil-in-Glycerin Emulsion; Lycopene

| Ingredient | % W/W |
|---|---|
| Glycerin | 67.0 |
| Medium chain tryglyceride (MCT) oil | 8.0 |
| Jojoba oil | 4.0 |
| Cetearyl-glucoside (Montanov 68) | 5.0 |
| Vit E | 0.5 |
| Lycopene (10% tomato extracted) | 0.5 |
| Water | 15.0 |

Example 13

Oil-in-Glycerin Emulsion; Aloe Vera

| Ingredient | % W/W |
|---|---|
| Glycerin | 59.3 |
| Medium chain tryglyceride (MCT) oil | 6.0 |
| Jojoba oil | 4.0 |
| Cetearyl-glucoside (Montanov 68) | 5.0 |
| Vit E | 0.5 |
| Aloe vera dry extract | 0.2 |
| Water | 25 |

Example 14

Oil-in-Glycerin Emulsion; Gingko

| Ingredient | % W/W |
|---|---|
| Glycerin | 57.0 |
| Medium chain tryglyceride (MCT) oil | 8.0 |
| Jojoba oil | 4.0 |
| Sorbitan ester (Span 80) | 2.0 |
| Glyceryl monostearate | 4.0 |
| Vit E | 0.5 |
| Gingko dry extract | 0.5 |
| Water | 24.0 |

Example 15

Oil-in-Glycerin Emulsion: Chinese Zizyphus

| Ingredient | % W/W |
|---|---|
| Glycerin | 57.0 |
| Medium chain tryglyceride (MCT) oil | 8.0 |
| Jojoba oil | 4.0 |
| Cetearyl-glucoside (Montanov 68) | 5.0 |
| Vit E | 0.5 |
| Chinese zizyphus jujuba extract | 0.5 |
| Water | 25 |

Example 16

Oil-in-Glycerin Emulsion; a Hydrophobic Peptide of 30 Amino

| Ingredient | % W/W |
|---|---|
| Glycerin | 63.5 |
| Medium chain tryglyceride (MCT) oil | 10.0 |
| Cetearyl-glucoside (Montanov 68) | 5.0 |
| Vit E | 0.5 |
| Peptide with hydrophobic domain | 1.0 |
| Water | 20 |

Example 17

Oil-in-Glycerin Emulsion; Anti-Inflammatory Peptide

| Ingredient | % W/W |
|---|---|
| Glycerin | 63.5 |
| Medium chain tryglyceride (MCT) oil | 10.0 |
| Cetearyl-glucoside (Montanov 68) | 5.0 |
| Vit E | 0.5 |
| Anti inflammatory peptide with hydrophobic domain | 1.0 |
| Water | 20 |

TABLE 4 example 17 anti-inflammatory effect of carrageennan injected rats paw edema volume at various mixing methods.

| Mixing method | Rats paw edema inflammation Volume |
|---|---|
| Magnetic stirrer | Largest (No activity or negligible) |
| High shear homogenizer | Median |
| High pressure homogenizer | Lowest |

Example 18

Oil-in-Glycerin Emulsion; Analgesic Peptide

| Ingredient | % W/W |
|---|---|
| Glycerin | 63.5 |
| Medium chain tryglyceride (MCT) oil | 10.0 |
| Cetearyl-glucoside (Montanov 68) | 5.0 |
| Vit E | 0.5 |
| Analgesic peptide with hydrophobic domain | 1.0 |
| Water | 20 |

TABLE 5

Example 18 analgesic effect in rats.

| Mixing method | Rats Hot Plate Response Time |
|---|---|
| Magnetic stirrer | Shortest, no effect |
| High shear homogenizer | Median |
| High pressure homogenizer | Longest |

Example 19

Oil-in-Glycerin Emulsion; Anti-Allergic Peptide

| Ingredient | % W/W |
|---|---|
| Glycerin | 63.5 |
| Medium chain tryglyceride (MCT) oil | 10.0 |
| Cetearyl-glucoside (Montanov 68) | 5.0 |
| Vit E | 0.5 |
| Anti-allergic peptide with hydrophobic domain | 1.0 |
| Water | 20 |

TABLE 5 example 19 anti-allergic effect in rats, erythema size in response to S.C. allergen injection and topical application of hydrophobic peptide with anti-allergic activity and various mixing method one hour prior to the allergen.

| Mixing method | Rats local dermal response to S.C. allergen, erythema size |
|---|---|
| Magnetic stirrer | Largest, no effect at all |
| High shear homogenizer | Median |
| High pressure homogenizer | Smallest |

Example 20

Fluorescein Dilaurate (FD) Oil-in-Glycerin Emulsion (OGE);

0.5 Fluorescein Dilaurate in nanometer OGE (FD SMOG) with mean droplet size of 0.6 microns was compared to 0.5% Fluorescein Dilaurate in OGE of 5 microns mean droplet size (FD OG) and 0.5% Fluorescein Dilaurate in vaselin (FD V). Samples were applied on shaved anaesthsized rats' abdomens and FD was extracted from skin samples after one and three hours and quantified by spectrofluorimeter as follows:

TABLE 6

Fluorescein Dilaurate levels in the skin in micrograms per square cm skin area at one and three hours after application of 0.5% Fluorescein Dilaurate in SM-OG versus OG versus Vaselin.

| | One Hour, mcg/cm$^2$ | Three Hours, mcg/cm$^2$ |
|---|---|---|
| FD SMOG | 42 | 83 |
| FD OG | 28 | 23 |
| FD V | 30 | 18 |

Fluorescein Dilaurate levels in the skin are larger when applied in SM-OG in comparison to the OG of the same formula but larger particles size and also in comparison to Vaselin.

Example 21

Oil-in-Glycerin Emulsion; Ceramides

| Ingredient | % W/W |
|---|---|
| Glycerin | 81.5 |
| Medium chain tryglyceride (MCT) oil | 6.0 |
| Sucrose ester (Sisterna S50C) | 6.0 |
| Ceramides | 4.0 |
| Vitamine E | 0.5 |

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A method for facilitating stratum corneum and dermal penetration of at least one bioactive agent having at least one hydrophobic moiety, the method comprising administering a topical cosmetic or pharmaceutical composition in the form of an oil-in-glycerin emulsion to a subject in need or desirous thereof, wherein said topical cosmetic or pharmaceutical composition comprises:

a continuous glycerin phase, wherein the continuous glycerin phase comprises at least 50% glycerin;

at least one oil comprising an internal phase, wherein the oil is present in an amount ranging from about 0.1-40 wt/wt %;

at least one emulsifying stabilizer, selected from the group consisting of saccharide esters or ethers, alkyl glucoside, sucrose esters, and sorbitan esters, wherein the emulsifying stabilizer is present in an amount ranging from about 0.1-10 wt/wt %; and the at least one bioactive agent comprising at least one hydrophobic moiety within its structure, wherein the at least one bioactive agent is present in an amount ranging from about 0.1-20 wt/wt %;

wherein the emulsion has a mean droplet size below one micron; and said topical cosmetic or pharmaceutical composition facilitates stratum-corneum and dermal penetration of said at least one bioactive agent.

2. A method according to claim 1, wherein the method is for the trans-dermal administration of the at least one bioactive agent.

3. A method according to claim 1, wherein the method is for the intra-dermal administration of the at least one bioactive agent.

4. A method according to claim 1, wherein the at least one bioactive agent is hydrophobic or amphiphilic, and is predominantly associated with the oily internal phase droplets.

5. A method according to claim 1, wherein the mean droplet size is between 100 and 1,000 nanometers.

6. A method according to claim 1, wherein the emulsifying stabilizer is made by condensation of at least one fatty acid or alcohol with a mono, di or poly saccharide.

7. A method according to claim 1, wherein the emulsifying stabilizer is made by condensation of at least one fatty acid or alcohol with a mono, di or poly saccharide and polyoxyethylene or polypropylene side chain.

8. A method according to claim 1, wherein the oil is present in an amount ranging from about 1-20 wt/wt %.

9. A method according to claim 1, wherein the emulsifying stabilizer is capable of forming a liquid crystal lamellar phase.

10. A method according to claim 1, wherein the glycerin constitutes a continuous phase of said emulsion and a minor portion of water is included in said glycerin phase.

11. A method according to claim 1, wherein the oil-in-glycerin emulsion is self-preserving and free of microbial preservatives.

12. A method according to claim 5, wherein mean nanometer droplet size is obtained solely by a process of mechanical mixing or high shear homogenization.

13. A method according to claim 1, wherein the at least one bioactive agent is selected from the group consisting of a botanical extract, a drug, a peptide, a polypeptide, a nucleotide and a glycolipid.

* * * * *